(12) United States Patent
Tybinkowski et al.

(10) Patent No.: US 9,208,918 B2
(45) Date of Patent: Dec. 8, 2015

(54) COMPUTERIZED TOMOGRAPHY (CT) IMAGING SYSTEM WITH MULTI-SLIT ROTATABLE COLLIMATOR

(71) Applicant: NeuroLogica Corp., Danvers, MA (US)

(72) Inventors: Andrew Tybinkowski, Boxford, MA (US); Lidia Nemirovsky, Salem, MA (US); Jack Tybinkowski, West Peabody, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

(21) Appl. No.: 14/083,207

(22) Filed: Nov. 18, 2013

(65) Prior Publication Data

US 2014/0140471 A1    May 22, 2014

Related U.S. Application Data

(60) Provisional application No. 61/727,436, filed on Nov. 16, 2012.

(51) Int. Cl.
| | |
|---|---|
| *A61B 6/06* | (2006.01) |
| *A61B 6/03* | (2006.01) |
| *G21K 1/02* | (2006.01) |

(52) U.S. Cl.
CPC . *G21K 1/02* (2013.01); *A61B 6/032* (2013.01); *A61B 6/035* (2013.01); *A61B 6/06* (2013.01)

(58) Field of Classification Search
CPC ........... G21K 1/043; G21K 1/04; G21K 1/02; G21K 1/025; G21K 1/046; G21K 1/10; A61B 6/06; A61B 6/032; A61B 6/027; A61B 6/03; A61B 6/0421; A61B 6/0457; A61B 6/08; A61B 6/14; A61B 6/4021; A61B 6/405; A61B 6/4275; A61B 6/467; A61B 6/482; A61B 6/488; A61B 6/505; A61B 6/547; A61B 6/548; A61B 6/583
USPC .......................... 378/147, 149, 150, 151, 153
See application file for complete search history.

(56) References Cited

U.S. PATENT DOCUMENTS

| | | | | |
|---|---|---|---|---|
| 4,277,685 | A * | 7/1981 | Covic et al. ...................... 378/7 |
| 4,304,999 | A * | 12/1981 | Richey et al. ..................... 378/4 |
| 4,380,820 | A * | 4/1983 | Cutter ........................... 378/153 |
| 4,419,764 | A * | 12/1983 | Kinanen ....................... 378/153 |
| 4,592,083 | A * | 5/1986 | O'Brien ........................ 378/160 |
| 4,672,648 | A * | 6/1987 | Mattson et al. .................... 378/4 |

(Continued)

FOREIGN PATENT DOCUMENTS

WO    WO 2012/106730    8/2012

*Primary Examiner* — David A Vanore
(74) *Attorney, Agent, or Firm* — Pandiscio & Pandiscio

(57) ABSTRACT

Apparatus for collimating an X-ray beam, the apparatus including a multi-slit rotatable collimator including a semi-tubular structure extending coaxially along a longitudinal axis and being formed out of an X-ray impermeable material, with at least two slits formed in the semi-tubular structure, wherein the at least two slits extend parallel to the longitudinal axis of the semi-tubular structure, a mount for rotatably supporting the semi-tubular structure in the path of an X-ray beam, and a drive mechanism for selectively rotating the semi-tubular structure about the longitudinal axis of the semi-tubular structure, whereby to selectively (i) position one slit in the path of the X-ray beam so as to tailor the X-ray beam to the width of that slit, and (ii) position a solid portion of the semi-tubular structure in the path of an X-ray beam so as to block an X-ray beam.

16 Claims, 15 Drawing Sheets

(56) References Cited

U.S. PATENT DOCUMENTS

| | | | |
|---|---|---|---|
| 4,995,066 A * | 2/1991 | Harding et al. | 378/146 |
| 5,054,041 A * | 10/1991 | Hampel | 378/4 |
| 5,090,037 A * | 2/1992 | Toth et al. | 378/4 |
| 5,225,980 A * | 7/1993 | Hsieh et al. | 378/18 |
| 5,835,555 A * | 11/1998 | Barry et al. | 378/146 |
| 6,157,696 A | 12/2000 | Saito et al. | |
| 6,272,206 B1 * | 8/2001 | Bjorkholm | 378/146 |
| 6,396,902 B2 | 5/2002 | Tybinkowski et al. | |
| 6,556,657 B1 | 4/2003 | Tybinkowski et al. | |
| 7,397,895 B2 | 7/2008 | Bailey et al. | |
| 7,706,508 B2 * | 4/2010 | Arenson et al. | 378/158 |
| 8,576,989 B2 * | 11/2013 | Kaminski | 378/160 |
| 2010/0119036 A1 * | 5/2010 | Muller | 378/38 |
| 2011/0002439 A1 | 1/2011 | Zhang | |
| 2012/0269319 A1 * | 10/2012 | Grodzins et al. | 378/51 |
| 2013/0064353 A1 * | 3/2013 | Al-Kofahi et al. | 378/147 |
| 2014/0146948 A1 * | 5/2014 | Zhang et al. | 378/147 |
| 2014/0177802 A1 * | 6/2014 | Zhao et al. | 378/87 |
| 2014/0270091 A1 * | 9/2014 | Nemeth et al. | 378/150 |

* cited by examiner

POSITION TO
EXPOSE SLIT
280A

POSITION TO
EXPOSE SLIT
280B

COMPUTERIZED TOMOGRAPHY (CT) IMAGING SYSTEM WITH MULTI-SLIT ROTATABLE COLLIMATOR

REFERENCE TO PENDING PRIOR PATENT APPLICATION

This patent application claims benefit of prior U.S. Provisional Patent Application Ser. No. 61/727,436, filed Nov. 16, 2012 by Andrew Tybinkowski et al. for COMPUTERIZED TOMOGRAPHY (CT) IMAGING SYSTEM WITH MULTI-SLIT ROTATABLE COLLIMATOR, which patent application is hereby incorporated herein by reference.

FIELD OF THE INVENTION

This invention relates to imaging systems in general, and more particularly to computerized tomography (CT) imaging systems.

BACKGROUND OF THE INVENTION

In many situations, it can be desirable to image the interior of opaque objects. By way of example but not limitation, in the medical field, it can be desirable to image the interior of a patient's body so as to allow viewing of internal body structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set and a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown a mobile CT imaging system 5 of the sort disclosed in U.S. Pat. No. 7,397,895, issued Jul. 8, 2008 to Eric M. Bailey et al. for MOBILE COMPUTERIZED TOMOGRAPHY (CT) IMAGING SYSTEM WITH CORDLESS AND WIRELESS CAPABILITIES, which patent is hereby incorporated herein by reference. Mobile CT imaging system 5 generally comprises a torus 10 which is supported by a base 15. Torus 10 and base 15 together comprise a frame for mobile CT imaging system 5. A center opening 20 is formed in torus 10. Center opening 20 receives the patient anatomy which is to be scanned.

Looking next at FIG. 3, torus 10 generally comprises an X-ray tube assembly 25, an X-ray detector assembly 30, and a rotating drum assembly 35. X-ray tube assembly 25 and X-ray detector assembly 30 are mounted to rotating drum assembly 35 in diametrically-opposing relation, such that an X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on rotating drum assembly 35 so that they are rotated concentrically about center opening 20, X-ray beam 40 will be passed through the patient's anatomy along a full range of radial positions, so as to enable mobile CT imaging system 5 to create a "slice" image of the anatomy penetrated by the X-ray beam. Furthermore, by moving mobile CT imaging system 5 relative to the patient during scanning, a series of slice images can be acquired, and thereafter appropriately processed, so as to create a 3D computer model of the scanned anatomy.

The various electronic hardware and software for controlling the operation of X-ray tube assembly 25, X-ray detector assembly 30, and rotating drum assembly 35, as well as for processing the acquired scan data so as to generate the desired slice images and 3D computer model, may be of the sort well known in the art and may be located in torus 10 and/or base 15.

Still looking now at FIG. 3, base 15 comprises a transport assembly 50 for moving mobile CT imaging system 5 relative to the patient. More particularly, as disclosed in the aforementioned U.S. Pat. No. 7,397,895, transport assembly 50 preferably comprises (i) a gross movement mechanism 55 for moving mobile CT imaging system 5 relatively quickly across room distances, so that the mobile CT imaging system can be quickly and easily brought to the "bedside" of the patient, and (ii) a fine movement mechanism 60 for moving the mobile CT imaging system precisely, relative to the patient, during scanning, so that the patient can be scanned at their bedside, without being moved. As discussed in U.S. Pat. No. 7,397,895, gross movement mechanism 55 preferably comprises a plurality of free-rolling casters, and fine movement mechanism 60 preferably comprises a plurality of centipede belt drives (which can be configured for either stepped or continuous motion, whereby to provide either stepped or continuous scanning). Hydraulic apparatus 65 permits either gross movement mechanism 55 or fine movement mechanism 60 to be engaged with the floor, whereby to facilitate appropriate movement of mobile CT imaging system 5.

Looking next at FIGS. 4 and 5, there is shown another mobile CT imaging system 105 of the sort disclosed in U.S. patent application Ser. No. 13/304,006, filed Nov. 23, 2011 by Eric M. Bailey et al. for ANATOMICAL IMAGING SYSTEM WITH CENTIPEDE SCANNING DRIVE, BOTTOM NOTCH TO ACCOMMODATE BASE OF PATIENT SUPPORT, AND MOTORIZED DRIVE FOR TRANSPORTING THE SYSTEM BETWEEN SCANNING LOCATIONS, which patent application is hereby incorporated herein by reference. Mobile CT imaging system 105 is generally similar to mobile CT imaging system 5 disclosed above, except that (i) mobile CT imaging system 105 is generally "scaled up" in size relative to mobile CT imaging system 5, (ii) a bottom notch 170 is provided in skirt 175 of mobile CT imaging system 105, and (iii) the casters of gross movement mechanism 55 of mobile CT imaging system 5 may be replaced by a pair of drive wheels 180A, 180B and a pair of casters 185A, 185B, and each of the centipede belt drives of fine movement mechanism 60 of mobile CT imaging system 5 may be replaced by a pair of parallel belt drives 190A, 190B disposed in side-by-side relation. Additional differences between mobile CT imaging system 105 of FIGS. 4 and 5 and mobile CT imaging system 5 of FIGS. 1-3 are disclosed in the aforementioned U.S. patent application Ser. No. 13/304,006.

For the purposes of the present invention, it is generally immaterial whether the present invention is used in conjunction with the aforementioned mobile CT imaging system 5, the aforementioned mobile CT imaging system 105 or another CT imaging system (e.g., a fixed position CT imaging system).

With all CT imaging systems (i.e., with the aforementioned mobile CT imaging system 5, the aforementioned mobile CT imaging system 105, or another CT imaging system such as a fixed position CT imaging system), it is generally necessary to collimate the X-ray beam emitted by the X-ray tube assembly before the X-ray beam passes through the body. More particularly, X-ray tube assemblies generally emit their X-rays in a broad, relatively unfocused pattern, and the anatomy is imaged in a slice fashion, so it is generally desirable to restrict the X-rays reaching the patient to only those X-rays which are actually used for the slices being imaged, and to block the remaining X-rays emitted by the X-ray tube assemblies. This is typically done with a collimator, which is essentially an X-ray shield having a slit formed therein, which is interposed between the X-ray tube assembly and the patient. In this way, the slit permits the "useful" X-rays (i.e., those being used for the slices being imaged) to reach the patient, while the body of the collimator blocks the remainder of the X-rays emitted by the X-ray tube assembly.

In addition to the foregoing, with "modern" CT imaging systems, it is possible to conduct multi-slice scanning of a patient by using a collimator having a slit wide enough to provide an X-ray beam which simultaneously encompasses multiple scan slices. In general, scanning with a wider X-ray beam (i.e., a higher slice count) yields faster scanning of a patient than scanning with a narrower X-ray beam (i.e., a lower slice count), but this is generally at the expense of subjecting the patient to a higher X-ray dose. For this reason, in some situations it may be desirable to make a high slice scan (e.g., a 32 slice scan) of a patient, whereas in other circumstances it may be desirable to make a low slice scan (e.g., an 8 slice scan) of a patient.

Since the width of the X-ray beam is determined by the width of the slit in the collimator, varying the slice count of the scan requires the use of a plurality of collimator slits each having different widths.

Thus there is a need for a fast, simple and reliable way to change collimator slits when the slice count of the scan is to be changed.

SUMMARY OF THE INVENTION

The present invention provides a fast, simple and reliable way to change collimator slits when the slice count of the scan is to be changed.

More particularly, the present invention comprises the provision and use of a novel multi-slit rotatable collimator, wherein each of the slits of the multi-slit rotatable collimator has a different size opening (i.e., each slit has a different width), and wherein the multi-slit collimator is rotated about an axis so as to selectively interpose a given slit between the X-ray tube assembly and the patient, whereby to allow scans of different slice counts to be made. In this way, the present invention provides a fast, simple and reliable way to change collimator slits when the slice count of the scan is to be changed.

Additionally, the multi-slit rotatable collimator may be rotated about an axis so as to not interpose a given slit between the X-ray tube assembly and the patient, whereby to selectively shield the patient from the X-rays generated by the X-ray tube assembly. In this way, the present invention provides a fast, simple and reliable way to shield the patient from the X-rays generated by the X-ray tube assembly.

In one preferred form of the invention, there is provided apparatus for collimating an X-ray beam, the apparatus comprising:

a multi-slit rotatable collimator comprising:
   a semi-tubular structure extending coaxially along a longitudinal axis, the semi-tubular structure being formed out of an X-ray impermeable material;
   at least one slit formed in the semi-tubular structure, wherein the at least one slit extends parallel to the longitudinal axis of the semi-tubular structure;
   a mount for rotatably supporting the semi-tubular structure in the path of an X-ray beam; and
   a drive mechanism for selectively rotating the semi-tubular structure about the longitudinal axis of the semi-tubular structure, whereby to selectively (i) position the at least one slit in the path of the X-ray beam so as to tailor the X-ray beam to the width of the at least one slit, and (ii) position a solid portion of the semi-tubular structure in the path of an X-ray beam so as to block an X-ray beam.

In another preferred form of the invention, there is provided apparatus for imaging a patient, the apparatus comprising:

a CT machine comprising an X-ray source; and
a multi-slit rotatable collimator comprising:
   a semi-tubular structure extending coaxially along a longitudinal axis, the semi-tubular structure being formed out of an X-ray impermeable material;
   at least one slit formed in the semi-tubular structure, wherein the at least one slit extends parallel to the longitudinal axis of the semi-tubular structure;
   a mount for rotatably supporting the semi-tubular structure in the path of the X-ray beam; and
   a drive mechanism for selectively rotating the semi-tubular structure about the longitudinal axis of the semi-tubular structure, whereby to selectively (i) position the at least one slit in the path of the X-ray beam so as to tailor the X-ray beam to the width of the at least one slit, and (ii) position a solid portion of the semi-tubular structure in the path of an X-ray beam so as to block an X-ray beam.

In another preferred form of the invention, there is provided a method for collimating an X-ray beam, the method comprising:

providing a multi-slit rotatable collimator comprising:
   a semi-tubular structure extending coaxially along a longitudinal axis, the semi-tubular structure being formed out of an X-ray impermeable material;
   at least one slit formed in the semi-tubular structure, wherein the at least one slit extends parallel to the longitudinal axis of the semi-tubular structure;
   a mount for rotatably supporting the semi-tubular structure in the path of an X-ray beam; and
   a drive mechanism for selectively rotating the semi-tubular structure about the longitudinal axis of the semi-tubular structure, whereby to selectively (i) position the at least one slit in the path of the X-ray beam so as to tailor the X-ray beam to the width of the at least one slit, and (ii) position a solid portion of the semi-tubular structure in the path of an X-ray beam so as to block an X-ray beam;
providing an X-ray beam; and
using the drive mechanism to selectively rotate the semi-tubular structure about the longitudinal axis of the semi-tubular structure.

In another preferred form of the invention, there is provided a method for imaging a patient, the method comprising:

providing a CT machine comprising an X-ray source, and a multi-slit rotatable collimator comprising a semi-tubular structure extending coaxially along a longitudinal axis, the semi-tubular structure being formed out of an X-ray impermeable material; at least one slit formed in the semi-tubular structure, wherein the at least one slit extends parallel to the longitudinal axis of the semi-tubular structure; a mount for rotatably supporting the semi-tubular structure in the path of the X-ray beam; and a drive mechanism for selectively rotating the semi-tubular structure about the longitudinal axis of the semi-tubular structure, whereby to selectively (i) position the at least one slit in the path of the X-ray beam so as to tailor the X-ray beam to the width of the at least one slit, and (ii) position a solid portion of the semi-tubular structure in the path of an X-ray beam so as to block an X-ray beam;

using the drive mechanism to selectively rotate the semi-tubular structure about the longitudinal axis of the semi-tubular structure; and scanning the patient using the CT machine.

BRIEF DESCRIPTION OF THE DRAWINGS

These and other features and advantages of the present invention will become more readily apparent during the following detailed description of the preferred embodiments of the invention, which is to be considered in conjunction with the accompanying drawings wherein like numbers refer to like parts and further wherein.

DETAILED DESCRIPTION OF THE PREFERRED EMBODIMENTS

Figure 1:
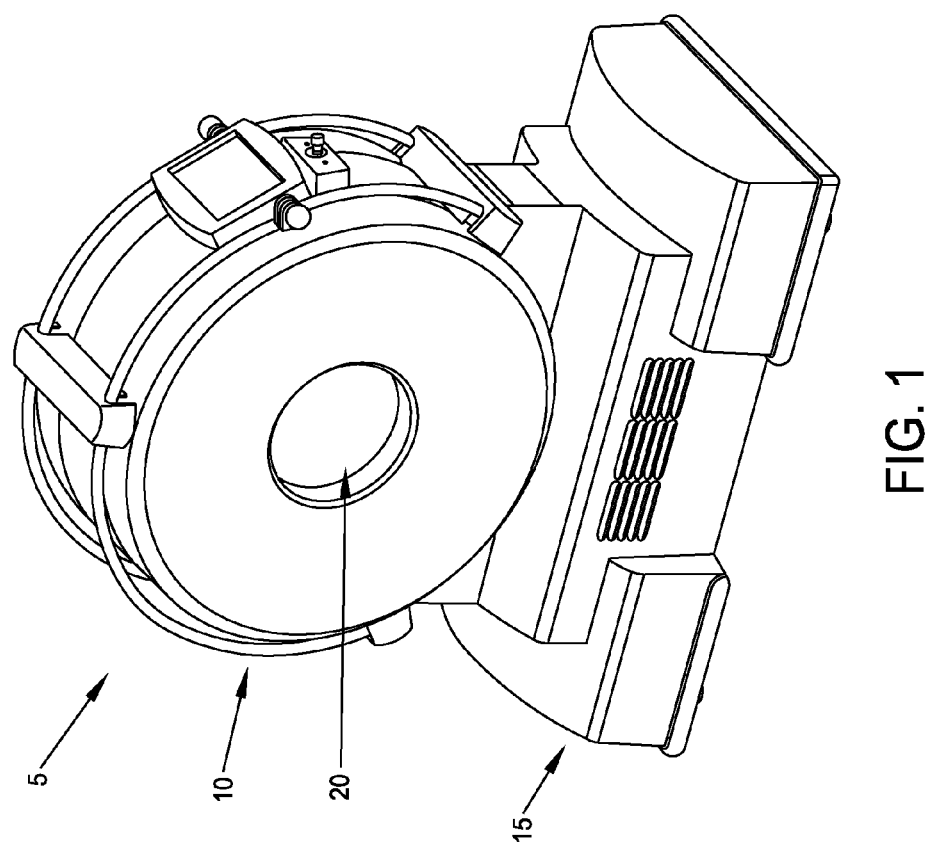
FIGS. 1-3 are schematic views showing an exemplary mobile CT imaging system.
Figure 2:
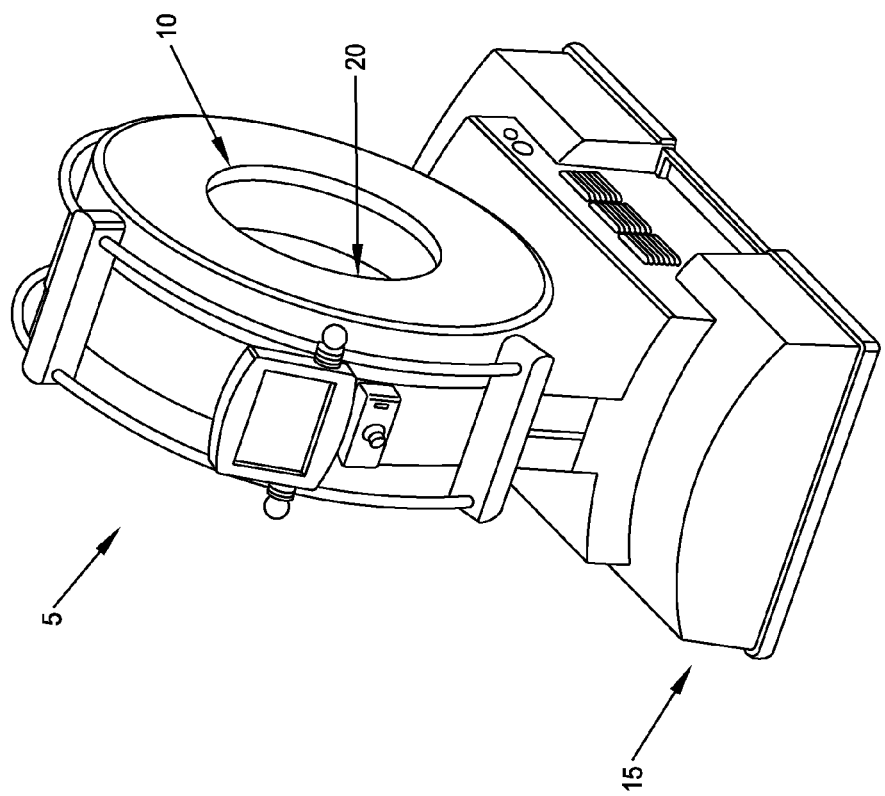
Figure 3:
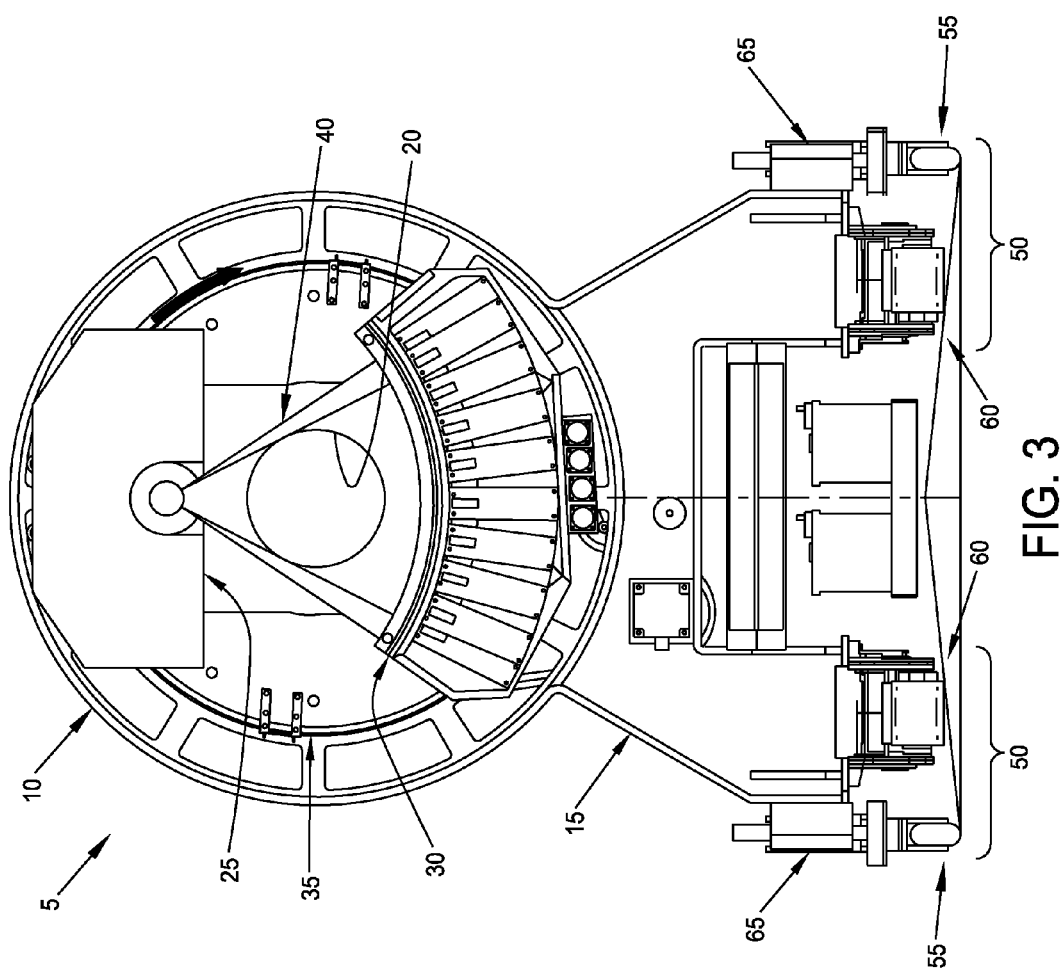
Figure 4:
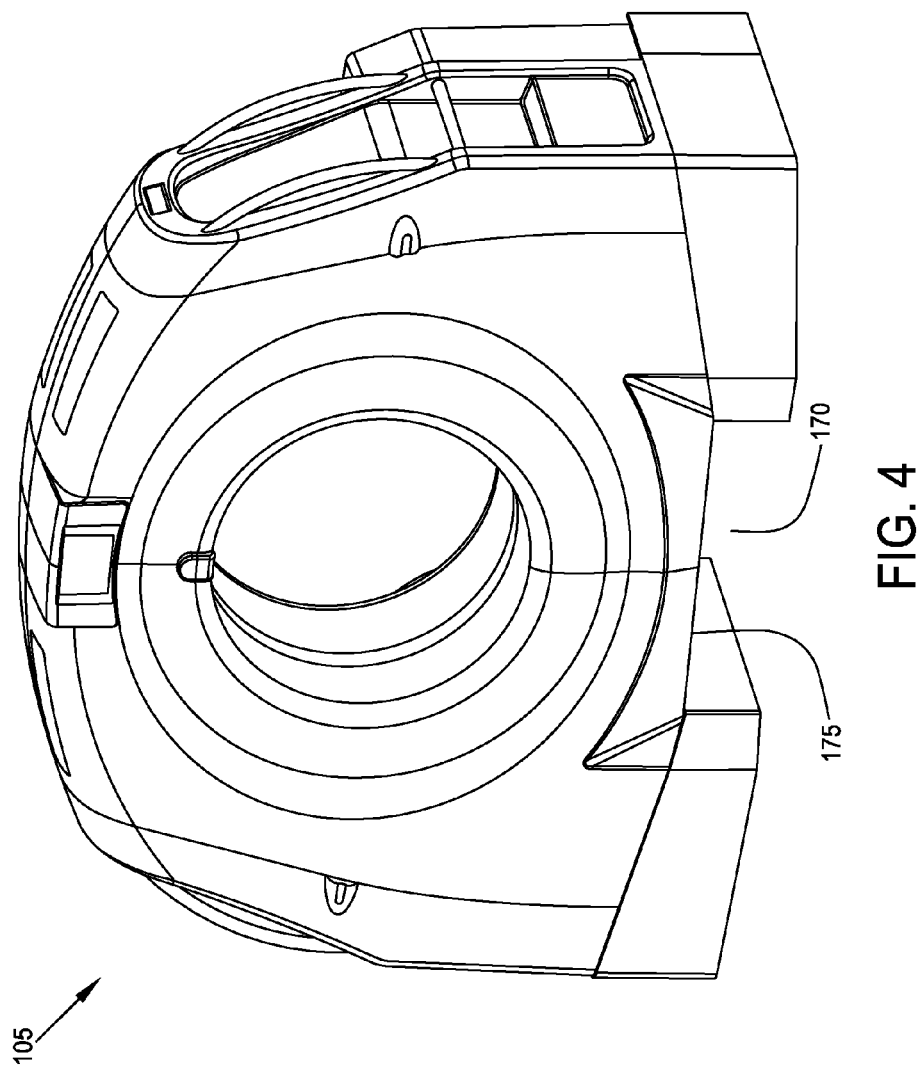
FIGS. 4 and 5 are schematic views showing another exemplary mobile CT imaging system.
Figure 5:
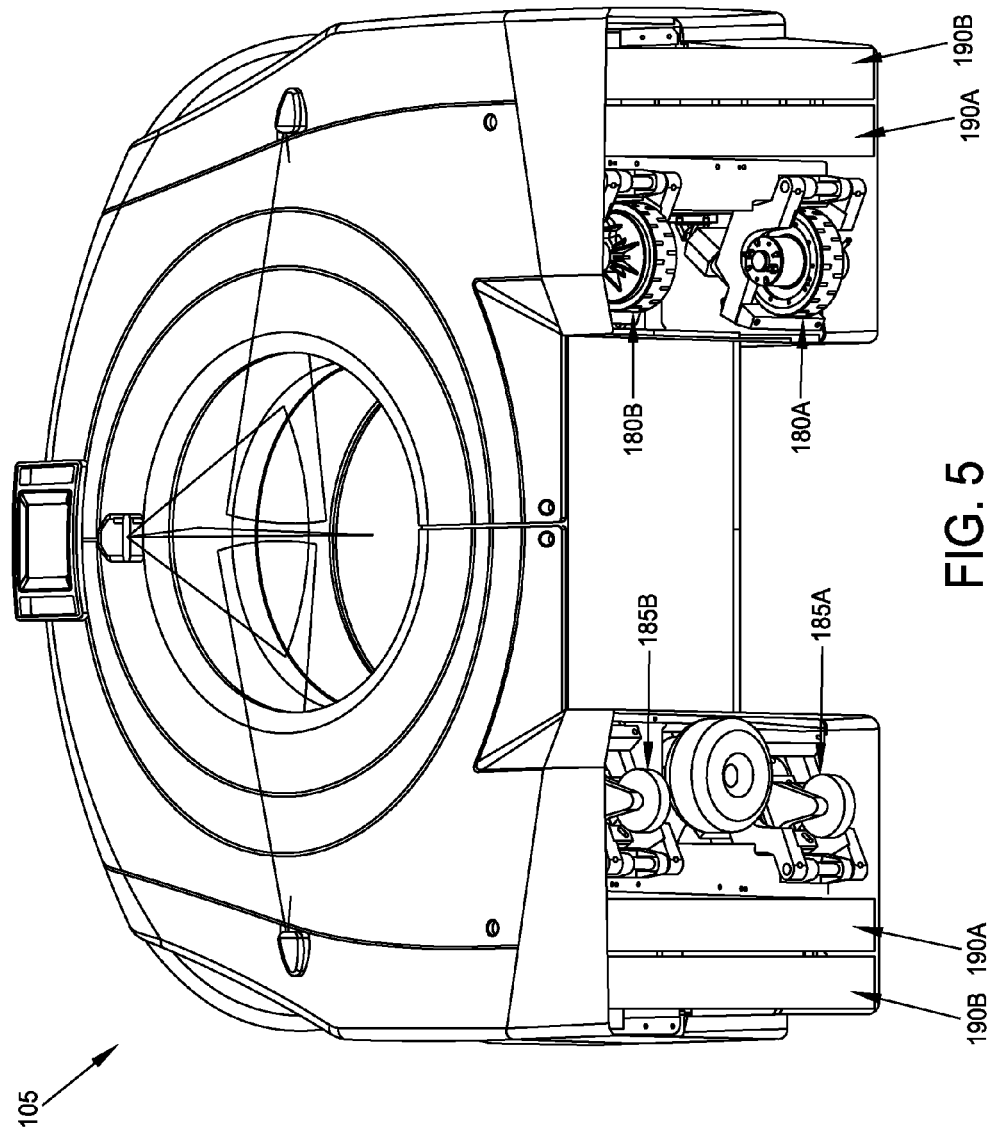
Figure 6:
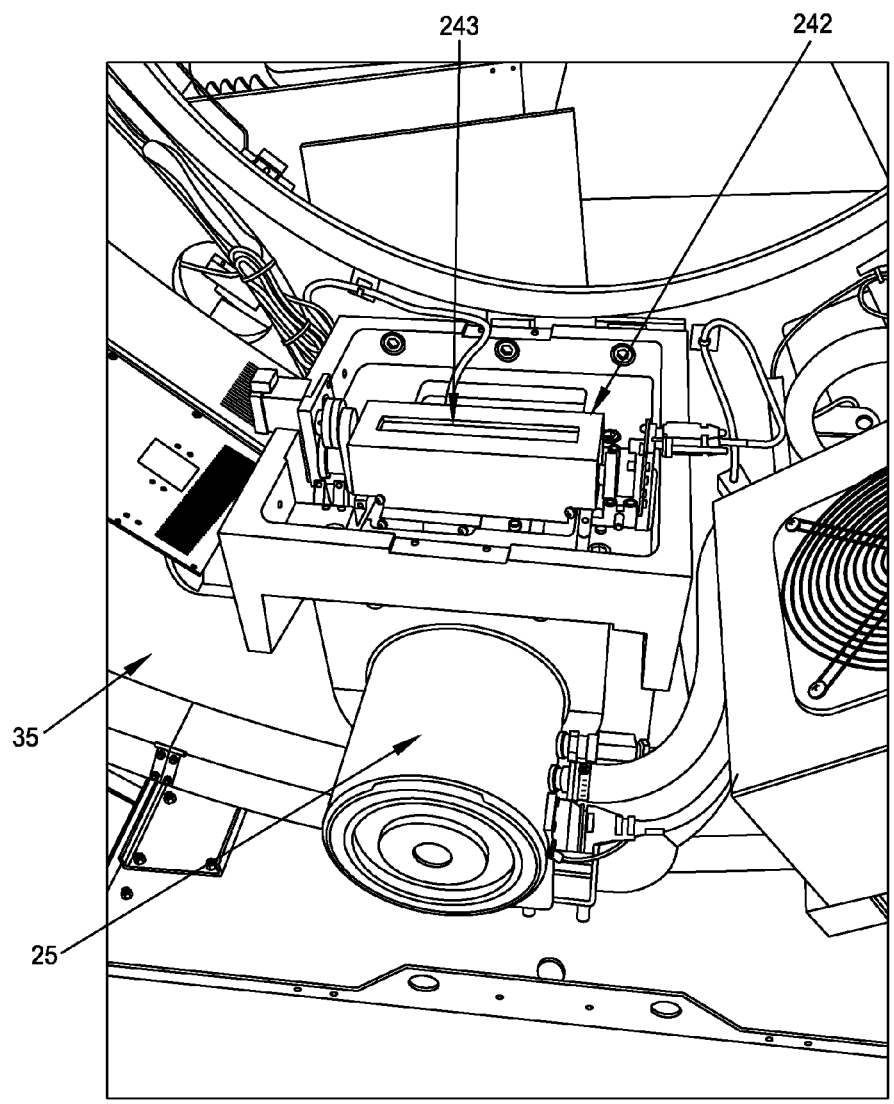
FIGS. 6-23 are schematic views showing a novel multi-slit rotatable collimator assembly formed in accordance with the present invention.
Figure 7:
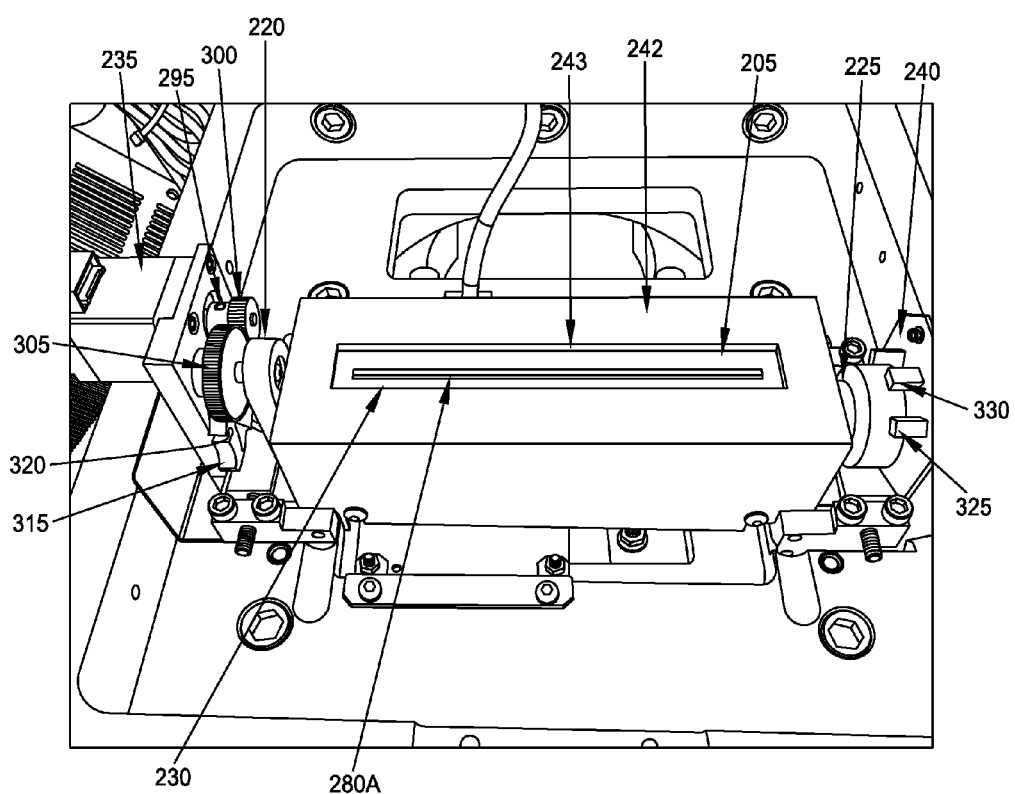
Figure 8:
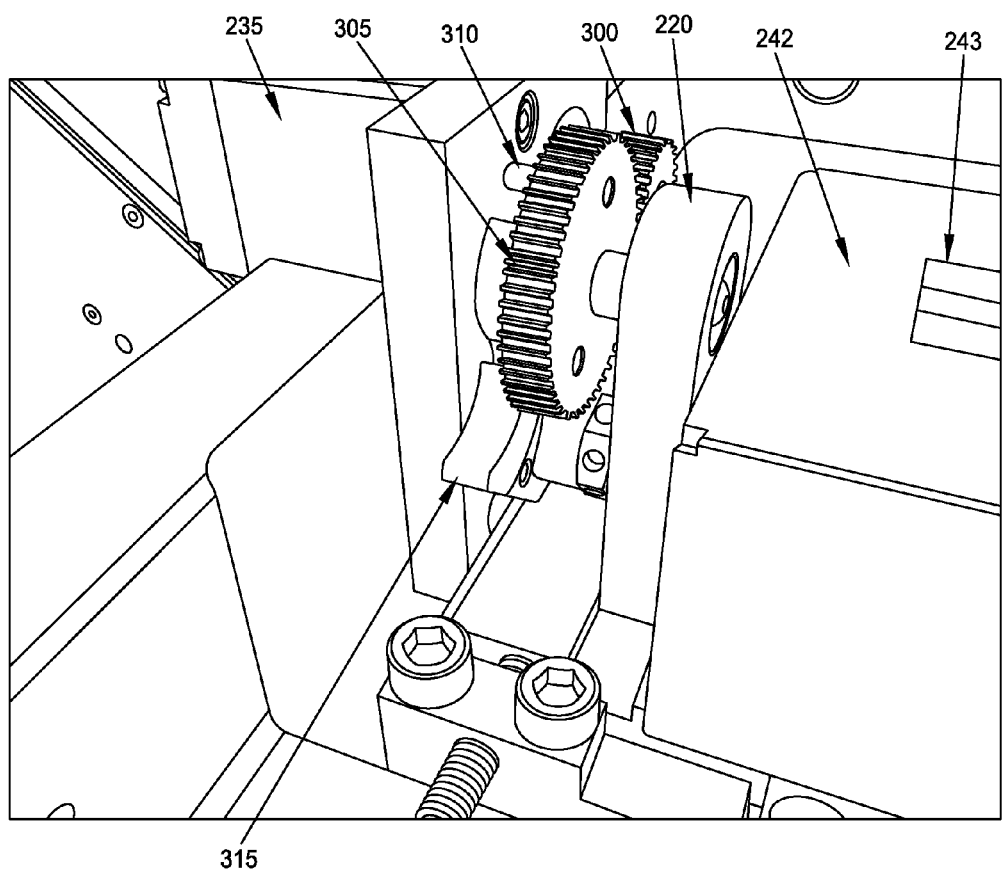
Figure 9:
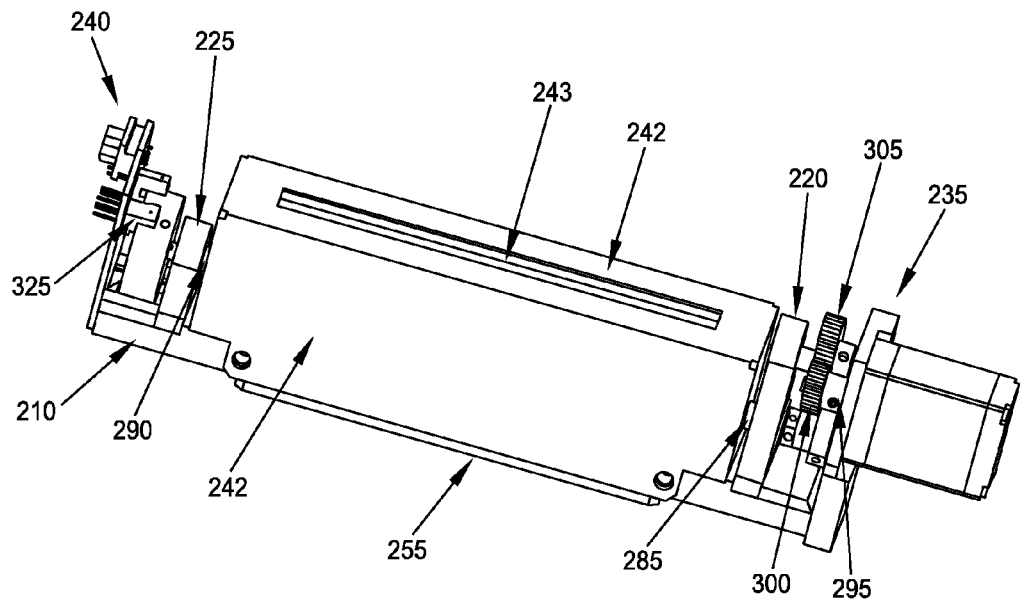
Figure 10:
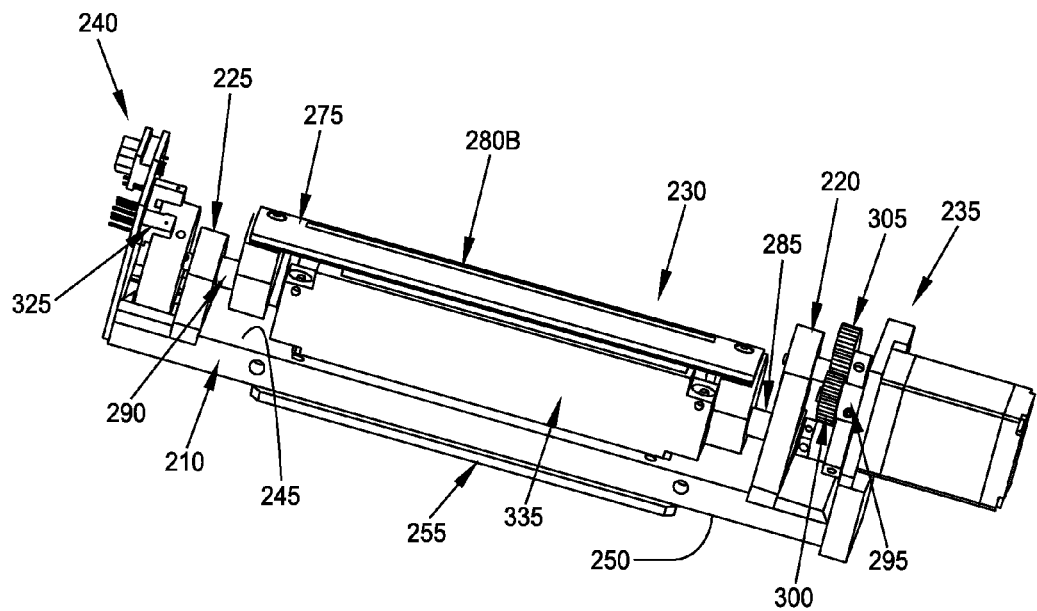
Figure 11:
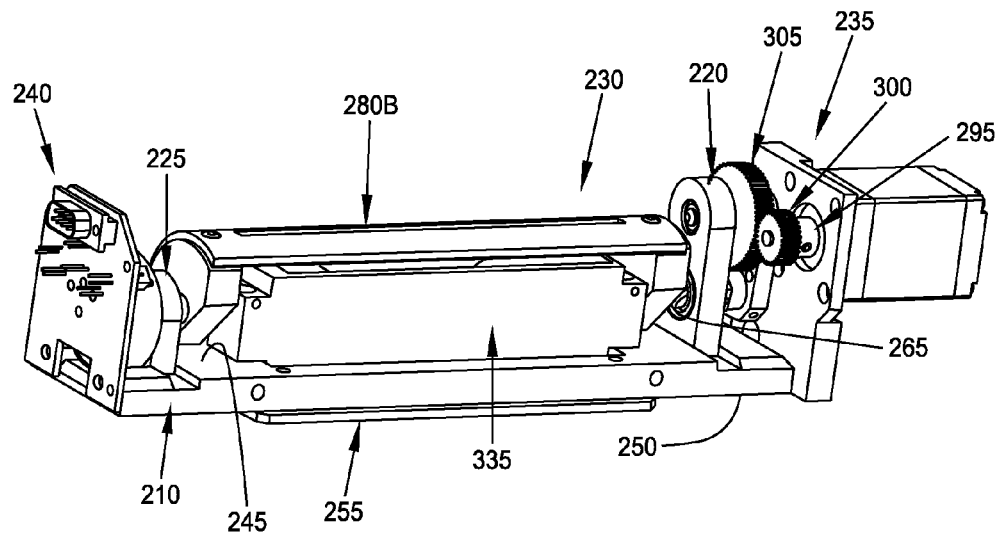
Figure 12:
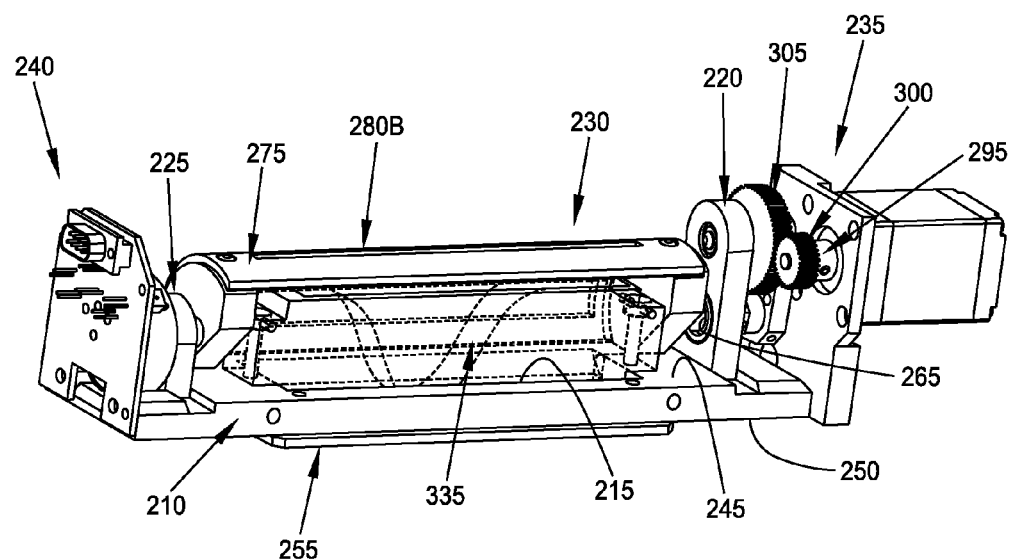
Figure 13:
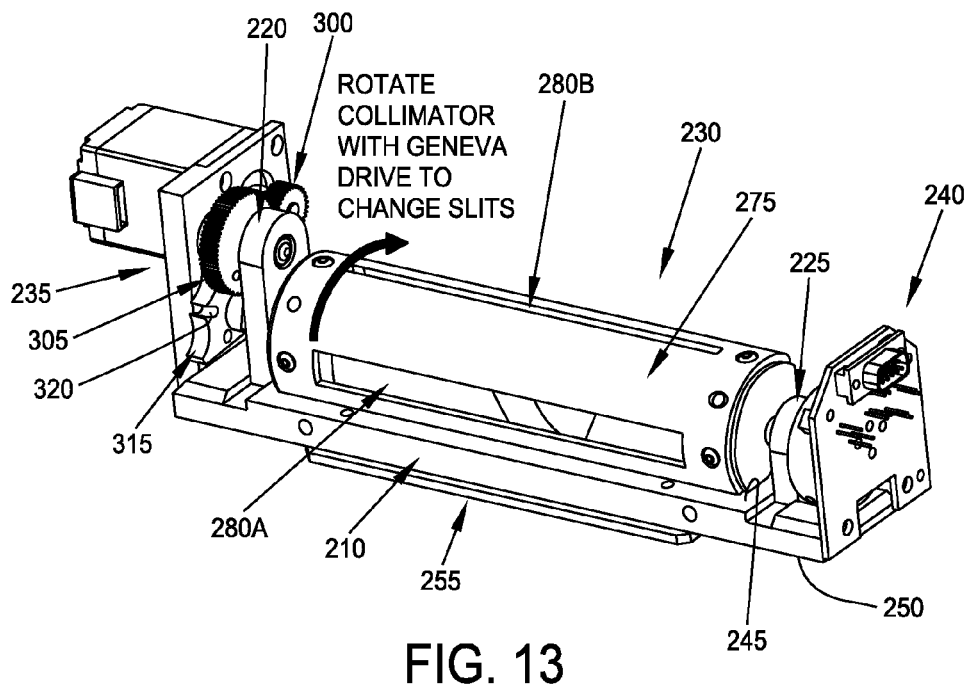
Figure 14:
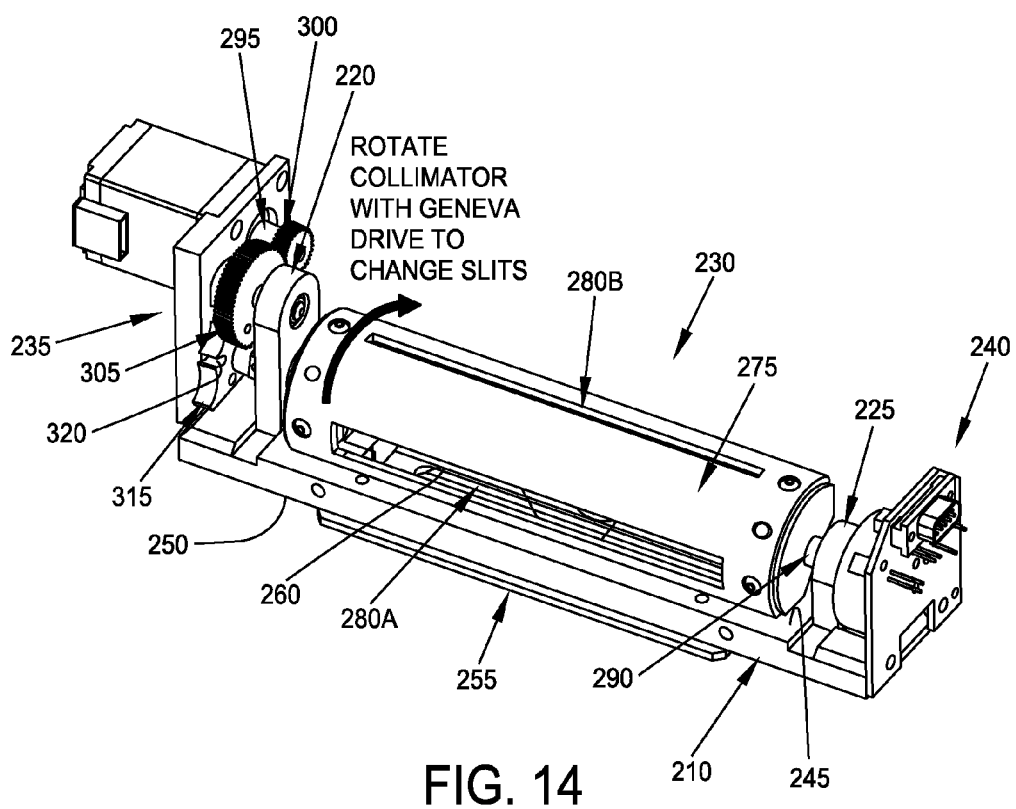
Figure 15:
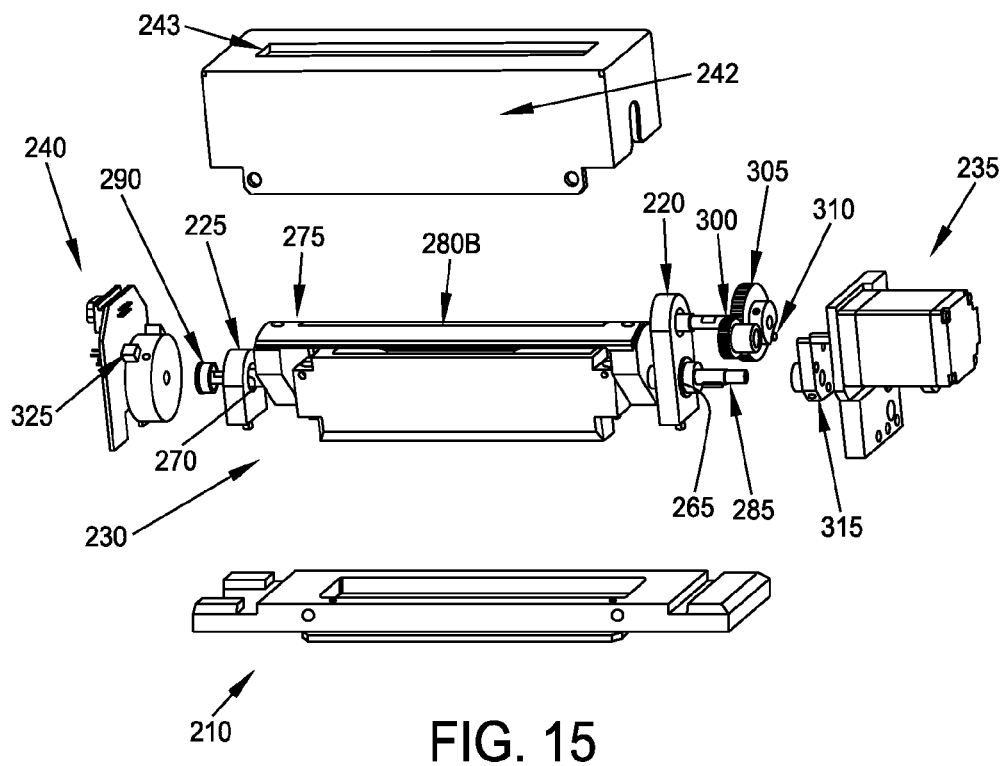
Figure 16:
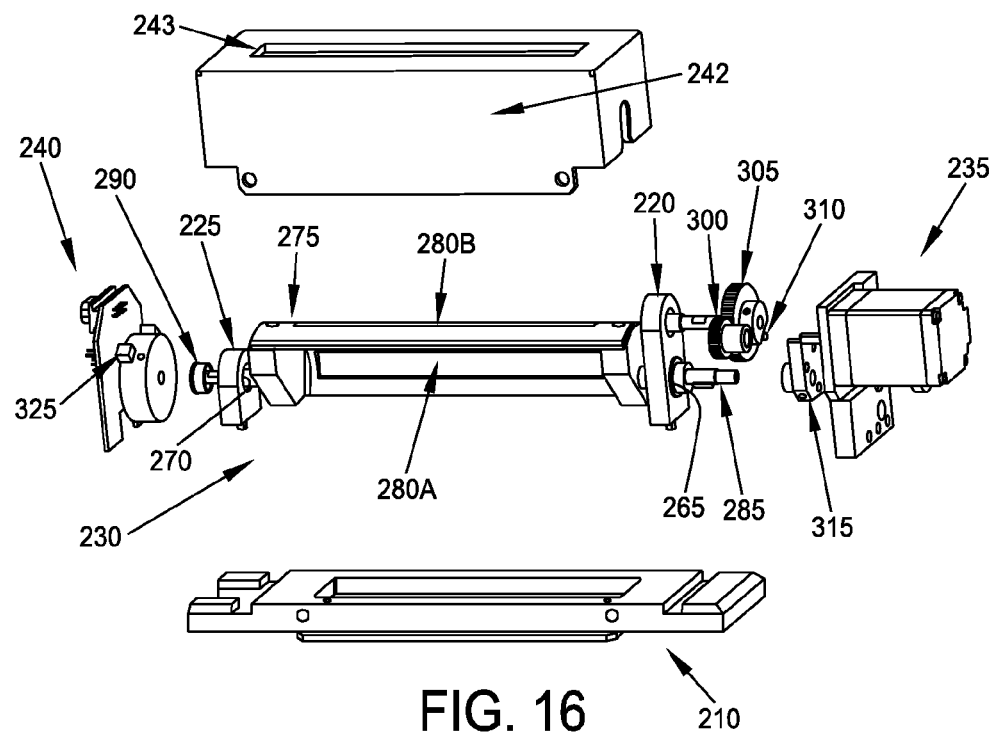

The present invention provides a fast, simple and reliable way to change collimator slits when the slice count of the scan is to be changed.

More particularly, the present invention comprises the provision and use of a novel multi-slit rotatable collimator, wherein each of the slits of the multi-slit rotatable collimator has a different size opening (i.e., each slit has a different width), and wherein the multi-slit collimator is rotated about an axis so as to selectively interpose a given slit between the X-ray tube assembly and the patient, whereby to allow scans of different slice counts to be made. In this way, the present invention provides a fast, simple and reliable way to change collimator slits when the slice count of the scan is to be changed.

Additionally, the multi-slit rotatable collimator may be rotated about an axis so as to not interpose a given slit between the X-ray tube assembly and the patient, whereby to selectively shield the patient from the X-rays generated by the X-ray tube assembly. In this way, the present invention provides a fast, simple and reliable way to shield the patient from the X-rays generated by the X-ray tube assembly.

In one preferred form of the invention, and looking now at FIGS. 6-23, there is provided a novel multi-slit rotatable collimator assembly 205 which generally comprises a base 210 having an opening 215, a pair of spaced supports 220, 225 mounted to base 210, a multi-slit rotatable collimator 230 rotatably mounted to supports 220, 225 so as to be movably disposed in front of opening 215, a drive mechanism 235 for rotating multi-slit rotatable collimator 230, and a position detector 240 for detecting the rotational disposition of multi-slit rotatable collimator 230. Preferably, multi-slit rotatable collimator assembly 205 is covered with a housing 242 having an opening 243, e.g., by securing housing 242 to base 210, with opening 243 in housing 242 being aligned with opening 215 in base 210.

More particularly, base 210 generally comprises a plate-like structure having an inner surface 245 and an outer surface 250. Opening 215 extends through base 210, opening on inner surface 245 and outer surface 250. A mounting plate 255 is preferably secured to outer surface 250 of base 210, whereby base 210 may be secured to the X-ray tube assembly of a CT imaging system, e.g., the X-ray tube assembly 25 of the aforementioned mobile CT imaging system 5, or the X-ray tube assembly of the aforementioned CT imaging system 105, or another CT imaging system such as a fixed position CT imaging system. Mounting plate 255 comprises an opening 260 (FIG. 14) aligned with opening 215 in base 210, whereby X-rays emitted from X-ray tube assembly 25 may pass through opening 260 in mounting plate 255 and through opening 215 in base 210.

Spaced supports 220, 225 are mounted to inner surface 245 of base 210 so that they reside on either end of opening 215. Spaced support 220 comprises an opening 265 (FIGS. 15 and 16), and spaced support 225 comprises an opening 270, wherein opening 265 in spaced support 220 is axially aligned with opening 270 in spaced support 225.

Multi-slit rotatable collimator 230 is rotatably mounted to supports 220, 225 so as to be movably disposed in front of opening 215. More particularly, multi-slit rotatable collimator 230 comprises a semi-tubular structure 275 (e.g., a 120 degree arc segment of a tube) formed out of an X-ray impermeable material (e.g., a high density material such as tungsten, molybdenum, etc.) having a plurality of longitudinal slits 280A, 280B, etc. formed therein, wherein each slit 280A, 280B, etc. has a different width (e.g., one slit 280A sized for a 32 slice scan, another slit 280B sized for an 8 slice scan, etc.). The two ends of semi-tubular structure 275 are movably mounted to spaced supports 220, 225 (e.g., by fitting axles 285, 290 through openings 265, 270 in spaced supports 220, 225, respectively) so that multi-slit rotatable collimator 230 may be rotated about its longitudinal axis, whereby to selectively position one of the slits 280A, 280B, etc. between X-ray tube assembly 25 and the patient, whereby to permit scans of different slice counts (e.g., 32 slice scans, 8 slice scans, etc.) to be made. Additionally, multi-slit rotatable collimator 230 may be rotated about its axis so as to not interpose a given slit 280A, 280B, etc. between the X-ray tube assembly and the patient, whereby to selectively shield the patient from the X-rays generated by the X-ray tube assembly.

Drive mechanism 235 is provided to selectively rotate multi-slit rotatable collimator 230 about its axis. Preferably semi-tubular structure 275 of multi-slit rotatable collimator 230 is rotated about its longitudinal axis using a Geneva drive mechanism, e.g., such as of the sort shown in FIG. 17-23. More particularly, drive mechanism 235 preferably comprises a drive shaft 295 which turns a gear 300, which in turn rotates a drive wheel 305 carrying a pin 310, which in turn rotates a driven wheel 315 having slots 320 therein. Driven wheel 315 is mounted to axle 285 extending through opening 265 in spaced support 220. Preferably the number and location of slots 320 in driven wheel 315 are coordinated with the number and location of slits 280A, 280B, etc. in semi-tubular structure 275, such that rotation of drive shaft 295 can selectively align a particular slit 280A, 280B, etc. with the X-ray beam emitted from X-ray tube assembly 25, whereby to selectively tailor the X-ray beam to a desired width. Furthermore, the number and location of slots 320 in driven wheel 315 are coordinated with the "solid" portions of semi-tubular structure 275, such that rotation of drive shaft 295 can selectively interpose a solid portion of semi-tubular structure 275 with the X-ray beam emitted from X-ray tube assembly 25, whereby to selectively block the X-ray beam emitted by X-ray tube assembly 25.

Figure 17:
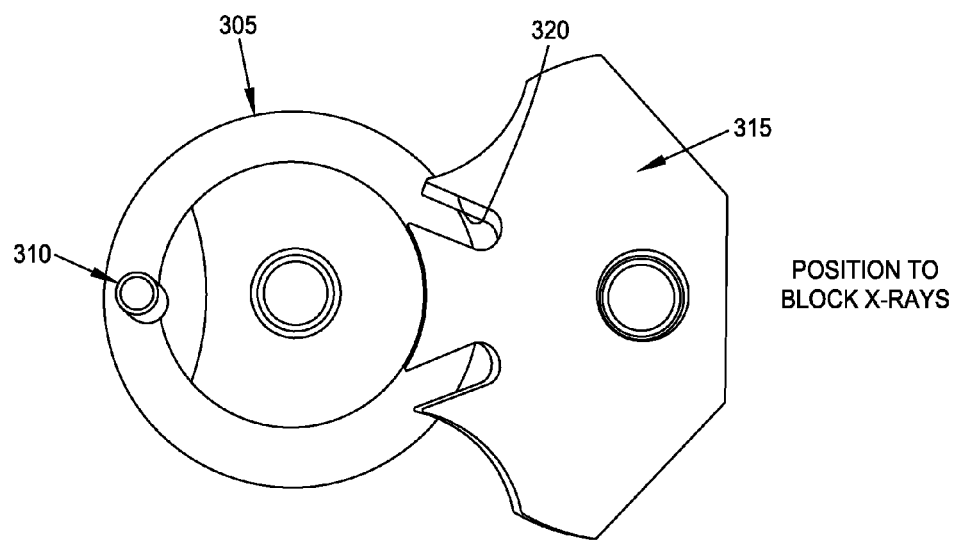
Figure 18:
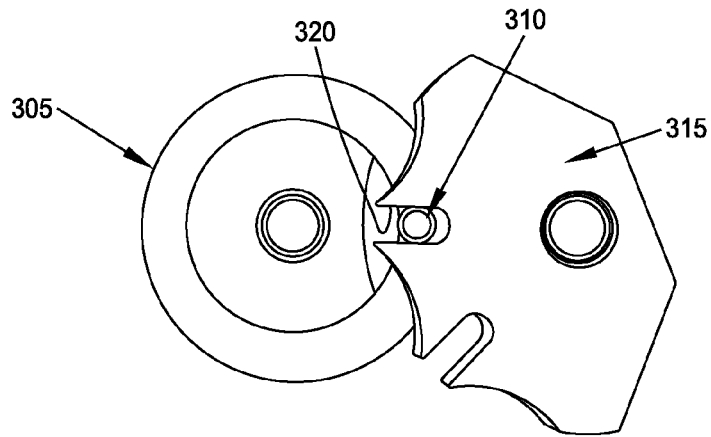
Figure 19:
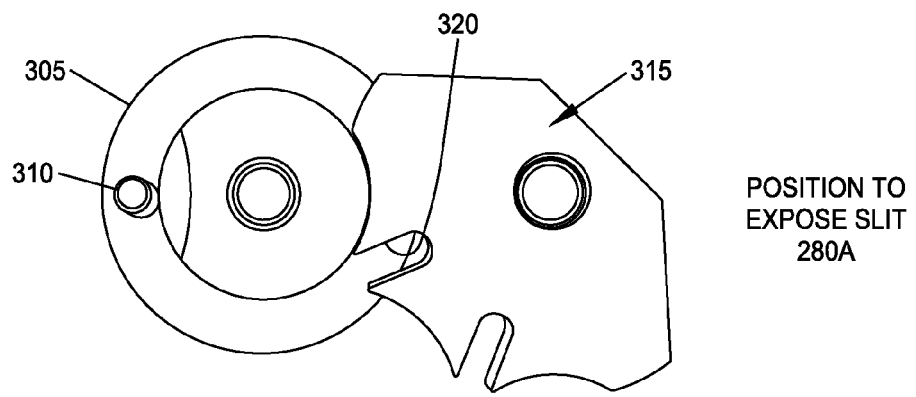
Figure 20:
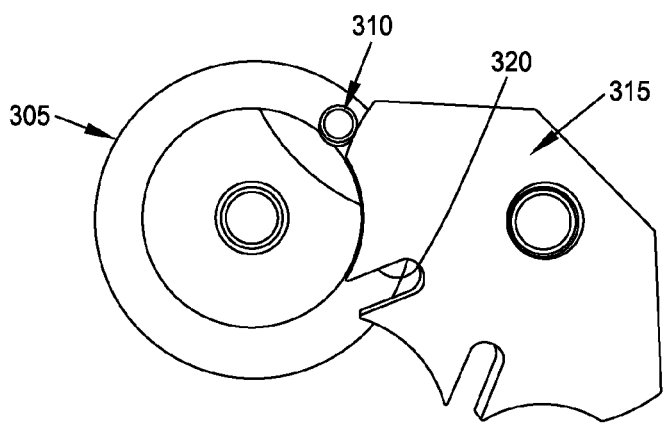
Figure 21:
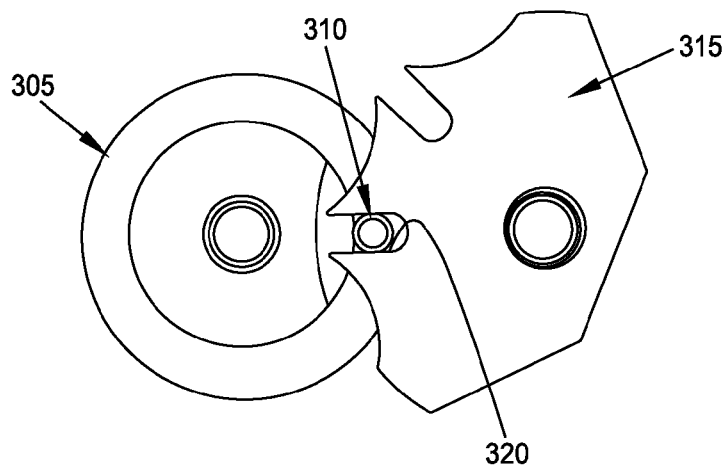
Figure 22:
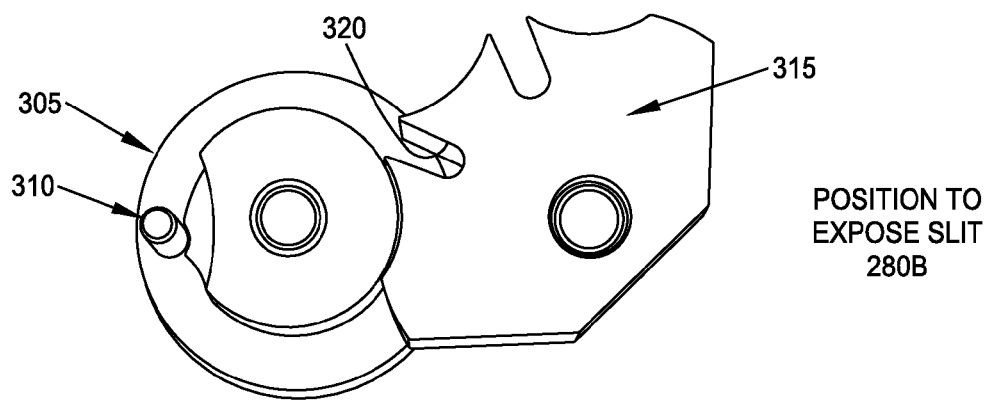
Figure 23:
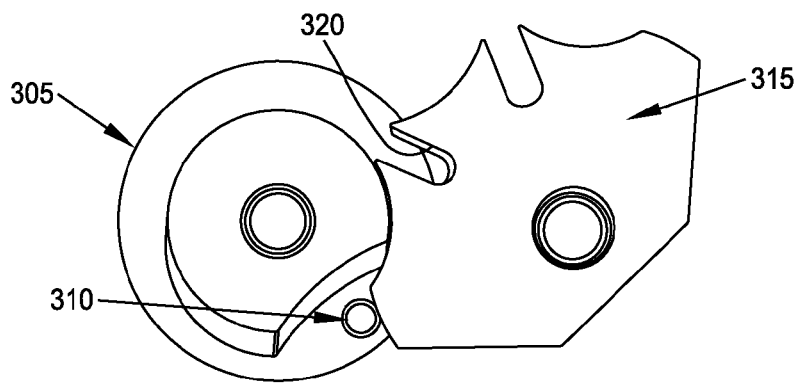

By way of example but not limitation, where semi-tubular structure 275 comprises a first slit 280A, a second slit 280B and a solid portion disposed between first slit 280A and second slit 280B, the Geneva drive mechanism may comprise a drive wheel 305 carrying a pin 310, which in turn rotates a driven wheel 315 having slots 320 therein, such that (i) the solid portion disposed between first slit 280A and second slit 280B will be presented to the X-ray beam when drive wheel 305 and driven wheel 315 are in the position shown in FIG. 17, (ii) slit 280A will be presented to the X-ray beam when drive wheel 305 and driven wheel 315 move through the positions shown in FIGS. 18-20, and (iii) slit 280B will be presented to the X-ray beam when drive wheel 305 and driven wheel 315 move through the positions shown in FIGS. 21-23.

Position detector 240 is provided for detecting the rotational disposition of multi-slit rotatable collimator 230. More particularly, position detector 240 comprises a sensor element 325 mounted to base 210, and a sensed element 330 mounted to axle 290 of multi-slit rotatable collimator 230, such that the rotational disposition of multi-slit rotatable collimator 230 can be determined using position detector 240.

As noted above, multi-slit rotatable collimator assembly 205 is preferably covered with housing 242 having opening 243 therein, e.g., by securing housing 242 to base 210, with opening 243 in housing 242 being aligned with opening 215 in base 210.

On account of the foregoing, when multi-slit rotatable collimator assembly 205 is mounted in front of the X-ray tube assembly of a CT imaging system so that X-rays emitted by the X-ray tube assembly pass through multi-slit rotatable collimator assembly 205, and when it is desired to scan a patient with an X-ray beam of a first slice width (e.g., a high slice scan such as a 32 slice scan), drive mechanism 235 is activated so as to turn multi-slit rotatable collimator 230 about its axis so as to position a first slit between X-ray assembly 25 and the patient (e.g., slit 280A). In this way multi-slit rotatable collimator 230 will tailor the width of the X-ray beam delivered to the patient to the desired first slice width.

Correspondingly, when it is desired to scan a patient with an X-ray beam of a second slice width (e.g., a low slice scan such as an 8 slice scan), drive mechanism 235 is activated so as to turn multi-slit rotatable collimator 230 about its axis so as to position a second slit between X-ray assembly 25 and the patient (e.g., slit 280B). In this way multi-slit rotatable collimator 230 will tailor the width of the X-ray beam delivered to the patient to the desired second slice width.

Furthermore, when it is desired to shield the patient from the X-ray beam emitted by X-ray assembly 25, drive mechanism 235 is activated so as to turn multi-slit rotatable collimator 230 about its axis so as to position a solid portion of semi-tubular structure 275 between X-ray assembly 25 and the patient. In this way multi-slit rotatable collimator 230 will block the X-ray beam from being delivered to the patient.

In one preferred form of the invention, multi-slit rotatable collimator 230 comprises two slits 280A, 280B, wherein slit 280A is sized to provide a 32 slice scan and slit 280B is sized to provide an 8 slice scan. However, if desired, more or less slits may be provided, and/or the widths of the slits may be varied. By way of example but not limitation, three slits 280A, 280B, 280C may be provided, with slit 280A being sized to provide a 64 slice scan, slit 280B being sized to provide an 32 slice scan and slit 280C being sized to provide an 8 slice scan. Still other configurations will be readily apparent to one skilled in the art in view of the present disclosure.

If desired, a filter may be interposed between X-ray assembly 25 and semi-tubular structure 275 of multi-slit rotatable collimator 230. By way of example but not limitation, a bow-tie filter 335 may be interposed between X-ray assembly 25 and semi-tubular structure 275 of multi-slit rotatable collimator 230. In one preferred form of the invention, bow-tie filter 335 (FIG. 12) is mounted to base 210 in front of opening 215 and within the volume defined by semi-tubular structure 275, such that X-rays emitted from X-ray assembly 25 are filtered prior to passing through a slit 280A, 280B, etc. in semi-tubular structure 275 or encountering a solid portion of semi-tubular structure 275.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for collimating an X-ray beam, the apparatus comprising:
   a multi-slit rotatable collimator comprising:
      a semi-tubular structure extending coaxially along a longitudinal axis, the semi-tubular structure being formed out of an X-ray impermeable material;
      at least two slits formed in the semi-tubular structure, wherein the at least two slits extend parallel to the longitudinal axis of the semi-tubular structure;
      a mount for rotatably supporting the semi-tubular structure in the path of an X-ray beam; and
      a drive mechanism for selectively rotating the semi-tubular structure about the longitudinal axis of the semi-tubular structure, whereby to selectively (i) position one of the at least two slits in the path of the X-ray beam so as to tailor the X-ray beam to the width of that slit, and (ii) position a solid portion of the semi-tubular structure in the path of an X-ray beam so as to block an X-ray beam;
   wherein the semi-tubular structure comprises two slits, and further wherein the drive mechanism is adapted to selectively rotate the semi-tubular structure about the longitudinal axis of the semi-tubular structure, whereby to selectively (a) position a first of the slits in the path of the X-ray beam so as to tailor the X-ray beam to the width of the first of the slits, (b) position the second of the slits in the path of the X-ray beam so as to tailor the X-ray beam to the width of the second of the slits, and (c) position a solid portion of the semi-tubular structure in the path of an X-ray beam so as to block an X-ray beam;
   wherein one of the two slits has a width greater than the other of the two slits; and
   wherein one of the two slits has a width configured to provide one of an 8 slice scan and a 32 slice scan.

2. Apparatus according to claim 1 wherein one of the two slits has a width configured to provide an 8 slice scan.

3. Apparatus according to claim 2 wherein the other of the two slits has a width configured to provide a 32 slice scan.

4. Apparatus according to claim 1 wherein the drive mechanism comprises a Geneva drive mechanism.

5. Apparatus according to claim 1 further comprising a position sensor for determining the rotational disposition of the semi-tubular structure relative to the mount.

6. Apparatus according to claim 1 further comprising a filter, wherein the filter is interposed between the X-ray beam and the semi-tubular structure.

7. Apparatus according to claim 6 wherein the filter comprises a bow-tie filter.

8. Apparatus for imaging a patient, the apparatus comprising:
a CT machine comprising an X-ray source; and
a multi-slit rotatable collimator comprising:
   a semi-tubular structure extending coaxially along a longitudinal axis, the semi-tubular structure being formed out of an X-ray impermeable material;
   at least two slits formed in the semi-tubular structure, wherein the at least two slits extend parallel to the longitudinal axis of the semi-tubular structure;
   a mount for rotatably supporting the semi-tubular structure in the path of an X-ray beam; and
   a drive mechanism for selectively rotating the semi-tubular structure about the longitudinal axis of the semi-tubular structure, whereby to selectively (i) position one of the at least two slits in the path of the X-ray beam so as to tailor the X-ray beam to the width of that slit, and (ii) position a solid portion of the semi-tubular structure in the path of an X-ray beam so as to block an X-ray beam;
   wherein the semi-tubular structure comprises two slits, and further wherein the drive mechanism is adapted to selectively rotate the semi-tubular structure about the longitudinal axis of the semi-tubular structure, whereby to selectively (a) position a first of the slits in the path of the X-ray beam so as to tailor the X-ray beam to the width of the first of the slits, (b) position the second of the slits in the path of the X-ray beam so as to tailor the X-ray beam to the width of the second of the slits, and (c) position a solid portion of the semi-tubular structure in the path of an X-ray beam so as to block an X-ray beam;
   wherein one of the two slits has a width greater than the other of the two slits; and
   wherein one of the two slits has a width configured to provide one of an 8 slice scan and a 32 slice scan.

9. Apparatus according to claim 8 wherein one of the two slits has a width configured to provide an 8 slice scan.

10. Apparatus according to claim 9 wherein the other of the two slits has a width configured to provide a 32 slice scan.

11. Apparatus according to claim 8 wherein the drive mechanism comprises a Geneva drive mechanism.

12. Apparatus according to claim 8 further comprising a position sensor for determining the rotational disposition of the semi-tubular structure relative to the mount.

13. Apparatus according to claim 8 further comprising a filter, wherein the filter is interposed between the X-ray beam and the semi-tubular structure.

14. Apparatus according to claim 13 wherein the filter comprises a bow-tie filter.

15. A method for collimating an X-ray beam, the method comprising:
providing a multi-slit rotatable collimator comprising:
   a semi-tubular structure extending coaxially along a longitudinal axis, the semi-tubular structure being formed out of an X-ray impermeable material;
   at least two slits formed in the semi-tubular structure, wherein the at least two slits extend parallel to the longitudinal axis of the semi-tubular structure;
   a mount for rotatably supporting the semi-tubular structure in the path of an X-ray beam; and
   a drive mechanism for selectively rotating the semi-tubular structure about the longitudinal axis of the semi-tubular structure, whereby to selectively (i) position one of the at least two slits in the path of the X-ray beam so as to tailor the X-ray beam to the width of that slit, and (ii) position a solid portion of the semi-tubular structure in the path of an X-ray beam so as to block an X-ray beam;
   wherein the semi-tubular structure comprises two slits, and further wherein the drive mechanism is adapted to selectively rotate the semi-tubular structure about the longitudinal axis of the semi-tubular structure, whereby to selectively (a) position a first of the slits in the path of the X-ray beam so as to tailor the X-ray beam to the width of the first of the slits, (b) position the second of the slits in the path of the X-ray beam so as to tailor the X-ray beam to the width of the second of the slits, and (c) position a solid portion of the semi-tubular structure in the path of an X-ray beam so as to block an X-ray beam;
   wherein one of the two slits has a width greater than the other of the two slits; and
   wherein one of the two slits has a width configured to provide one of an 8 slice scan and a 32 slice scan;
providing an X-ray beam; and
using the drive mechanism to selectively rotate the semi-tubular structure about the longitudinal axis of the semi-tubular structure.

16. A method for imaging a patient, the method comprising:
providing a CT machine comprising an X-ray source, and a multi-slit rotatable collimator comprising a semi-tubular structure extending coaxially along a longitudinal axis, the semi-tubular structure being formed out of an X-ray impermeable material; at least two slits formed in the semi-tubular structure, wherein the at least two slits extend parallel to the longitudinal axis of the semi-tubular structure; a mount for rotatably supporting the semi-tubular structure in the path of the X-ray beam; and a drive mechanism for selectively rotating the semi-tubular structure about the longitudinal axis of the semi-tubular structure, whereby to selectively (i) position one of the at least two slits in the path of the X-ray beam so as to tailor the X-ray beam to the width of that slit, and (ii) position a solid portion of the semi-tubular structure in the path of an X-ray beam so as to block an X-ray beam; wherein the semi-tubular structure comprises two slits, and further wherein the drive mechanism is adapted to selectively rotate the semi-tubular structure about the longitudinal axis of the semi-tubular structure, whereby to selectively (a) position a first of the slits in the path of the X-ray beam so as to tailor the X-ray beam to the width of the first of the slits, (b) position the second of the slits in the path of the X-ray beam so as to tailor the X-ray beam to the width of the second of the slits, and (c) position a solid portion of the semi-tubular structure in the path of an X-ray beam so as to block an X-ray beam; wherein one of the two slits has a width greater than the other of the two slits; and wherein one of the two slits has a width configured to provide one of an 8 slice scan and a 32 slice scan;
using the drive mechanism to selectively rotate the semi-tubular structure about the longitudinal axis of the semi-tubular structure; and
scanning the patient using the CT machine.

* * * * *